United States Patent [19]

Feinstein et al.

[11] 4,094,912

[45] June 13, 1978

[54] PROCESS FOR CONVERTING AROMATIC ALDEHYDES TO PHENOLIC COMPOUNDS

[75] Inventors: Allen I. Feinstein, Wheaton; Shantaram G. Kane, Naperville; Ellis K. Fields, River Forest, all of Ill.

[73] Assignee: Standard Oil Company (Indiana), Chicago, Ill.

[21] Appl. No.: 738,084

[22] Filed: Nov. 2, 1976

[51] Int. Cl.² ............................................. C07C 39/04
[52] U.S. Cl. .................................... 568/802; 568/800; 368/798; 568/733; 568/741; 568/747
[58] Field of Search ........... 260/621 G, 621 R, 624 R, 260/600, 620, 619 F

[56] References Cited

U.S. PATENT DOCUMENTS

| | | | |
|---|---|---|---|
| 3,850,995 | 11/1974 | Horlenko et al. | 260/621 G |
| 3,962,350 | 6/1976 | Horlenko et al. | 260/621 |

*Primary Examiner*—James O. Thomas, Jr.
*Assistant Examiner*—Werren B. Lone
*Attorney, Agent, or Firm*—William C. Clarke; Arthur G. Gilkes; William T. McClain

[57] ABSTRACT

Aromatic aldehydes wherein the aldehyde group is directly attached to the aromatic ring are oxidized directly to phenolic compounds in the vapor phase. Tar and carbonaceous product formation are minimized by the method of preheating and mixing the reactants and by a rapid reaction temperature quench of the reaction mixture to below 0° C. Mixing temperature is 300°–350° C. and reaction temperature is 400°–600° C. at 1–10 atmosphere pressure.

11 Claims, No Drawings

PROCESS FOR CONVERTING AROMATIC ALDEHYDES TO PHENOLIC COMPOUNDS

BACKGROUND OF THE INVENTION

The field of this invention relates to an improved method for the direct vapor-phase oxidation of aromatic aldehydes to phenolic compounds.

The direct vapor-phase oxidation of benzaldehyde to phenol is known. U.S. Pat. No. 3,850,995 to Horlenko et al. teaches the vapor phase preparation of phenol from benzaldehyde by reacting benzaldehyde with oxygen at a temperature of 250° to 450° C. According to the patentee, excessive amounts of tar were found to occur unless precautions were taken. Methods of alleviating the formation of tars and carbonaceous compounds concerned the use of a hydrocarbon diluent such as benzene and toluene.

The disadvantages of using a hydrocarbon diluent are: (1) in a diluted reaction regime, a larger residence time is required as compared to an undiluted regime to produce a given amount of product, (2) the unreacted hydrocarbon diluent must be separated from the product at the completion of the reaction. This separation entails an extra processing step.

We have found that the operating difficulties caused by the formation of tars and carbonaceous materials can be avoided by the process of our invention, i.e., (1) the method and temperature of mixing the reactant aromatic aldehyde with an oxygen-containing gas, (2) the temperature and residence time of the reactants in the reactor and (3) the method and temperature of the reaction quench following the reaction. A hydrocarbon diluent is not necessary.

It is, therefore, an object of the present invention to provide a method of converting an aromatic aldehyde to the corresponding phenolic compound in high yield without the necessity of using a hydrocarbon diluent. It is another object to provide an economical method for accomplishing such conversion over present methods by reducing formation of benzoic acid and by eliminating the need for separating a hydrocarbon diluent from product. Other objects of the invention will be apparent from the following detailed description and examples.

BRIEF SUMMARY OF THE INVENTION

This invention relates to a continuous process for converting a aromatic aldehyde to a phenolic compound by contacting a preheated gaseous aldehyde at from about 300° to 350° C with an oxygen-containing gas in a stream of an inert gas and reacting said aldehyde and said oxygen-containing gas at a temperature of from about 400° to 600° C in the vapor phase at one to ten atmospheres pressure and wherein said reactants are cooled to a temperature of from about 0° to −80° C. upon leaving the reactor.

DETAILED DESCRIPTION OF INVENTION

It has been found in accordance with this invention that aromatic aldehydes, particularly benzaldehyde, can be oxidized in the vapor phase in the presence of oxygen-containing gas to phenolic compounds in good yield without the need of catalyst or hydrocarbon diluent. Tar formation can be reduced by pre-mixing the feed streams at a temperature of from 300° to 350° C. prior to being fed into the reactor, reacting the mixed stream at reaction temperatures of 400° to 600° C. and immediately quenching the reaction at a temperature within the range of from 0° to −80° C.

For purposes of this invention the term "aromatic aldehyde" is defined as a class of organic compounds of the chemical formula RCHO where —CHO is an aldehyde group directly attached to the aromatic ring. R is a radical of a carbocyclic compound of aromatic character such as phenyl, naphthyl radicals. R can be substituted with individually selected substituents such as alkyl moieties containing up to 4 carbons, including methyl, ethyl, propyl, butyl, and iso-, secondary and tertiary alkyls such as isopropyl, t-butyl; alkoxy such as —$OCH_3$, —$OCH_2CH_3$, etc.; hydroxyalkyl such as —$CH_2OH$, —$CH_2CH_2OH$, etc.; oxoalkyl such as —$COCH_3$, —$COCH_2CH_3$, etc. The number of substituents apart from hydrogen can be from 1 to 5. Hydrogen moieties fulfill the remaining unsubstituted positions of the radical R.

The aromatic radicals R are selected from radicals derived from benzene, fused aromatic compounds and polyphenyl compounds. Fused carbocyclic compounds up to three rings can be selected; preferred are those having 2 rings with up to 10 carbon ring-atoms. Such fused aromatic compounds include naphthalene, anthracene and phenanthrene. Polyphenyl structures preferred are those from bi-phenyl and tri-phenyl.

The term "phenolic compound" is defined as a class of organic compounds of the chemical formula ROH where —OH is a hydroxy group and R is defined as above. Examples of phenolic compounds are phenol, the cresols, resorcinol, the xylenols, etc. The term "oxygen-containing gas" is defined as any gas containing oxygen including molecular oxygen, air, etc. For convenience, the term "oxygen" will be used to designate the oxygen in the oxygen-containing gas and the molecular oxygen required for the reaction.

The present invention relates to a process for the oxidation of an aromatic aldehyde to a phenolic compound which consists essentially of (1) premixing the gaseous reactants, the aldehyde and the oxygen, the oxygen being mixed with an inert diluent in a concentration sufficient to avoid forming an explosive mixture, at a temperature of from 300° to 350° C., the said diluent present in a mole ratio within the range from about 2.0 to 50 moles per mole of aldehyde, (2) introducing the reactants into the reactor at pressures of from one to ten atmospheres, and causing the said reactants to be in contact at temperatures of from 400° to 600° C in the vapor phase, the said reactants in mole ratios oxygen to aldehyde of from 0.4 to 1 to 40 to 1 with a residence time of 1 to 10 seconds, followed by (3) quenching the reaction mixture at a temperature of from about 0° to −80° C.

The continuous oxidation of benzaldehyde to phenol can be carried out in the absence of a catalyst or a hydrocarbon diluent by reacting pre-heated benzaldehyde with oxygen, the oxygen containing an inert diluent, in the vapor phase at temperatures of from 400° to 600° C. By pre-heating the benzaldehyde and an oxygen-inert gas mixture separately to a temperature of 300°–350° C. in a preheat section and by rapidly mixing the oxygen-inert gas mixture with the benzaldehyde and then introducing the mixture into the reactor at a temperature of from 400° to 600° C., and by quenching the reaction mix at a temperature of from 0° to −80° C., benzaldehyde is converted to phenol in high yields.

For the continuous process contemplated, a properly proportioned mixture of aromatic aldehyde and oxygen, the oxygen either in an oxygen-containing gas containing an inert diluent or mixed with an inert diluent prior to contacting the said aldehyde, is passed through a reactor which has been heated to the desired temperature in such a manner that the heat of the exothermic reaction can be dissipated so as to maintain a uniform temperature profile in the reactor. The reactor can be tubular or back-mixed in design. The reaction is carried out at atmospheric pressure although it can be carried out at pressures up to 10 atmospheres. The phenol is separated and recovered from the gaseous and other products by standard methods such as fractional distillation and solvent extraction. The unreacted benzaldehyde can be separated from the product and subsequently recycled back to the reactor also by standard methods such as fractional distillation and solvent extraction. Suitable solvents include water, alcohols such as methyl, ethyl, isopropyl alcohols, and glycols and ethers including dioxane.

A gas containing molecular oxygen or molecular oxygen can be used in the oxidation process. The oxidation can be carried out with molecular oxygen in the range of about 0.4 to about 40 moles per mole of benzaldehyde, (excluding oxygen to benzaldehyde mole ratios which fall within the explosive range). The preferred amount of oxygen will range from about 0.4 to 3.0 moles per mole of aromatic aldehyde charged.

The reaction is moderated by the use of a suitable inert gaseous diluent which can consist of nitrogen, argon, steam or carbon dioxide or a mixture thereof. Nitrogen or steam are preferable because of easy availability. The amount of diluent required will be from 2 to about 50 moles of benzaldehyde charged, preferably from 2 to 20 moles of benzaldehyde.

It is our view that the mechanism of the oxidation reaction using benzaldehyde as the carbocyclic aromatic aldehyde, as represented by the following equations, will explain the observed products. However, the process of this invention is not to be bound by or restricted to this mechanism.

(1) $C_6H_5CHO + O_2 \rightarrow C_6H_5CO\cdot + HO_2\cdot$
(2) $C_6H_5CO\cdot \rightarrow C_6H_5\cdot + CO$
(3) $C_6H_5\cdot + O_2 \rightarrow C_6H_5OO\cdot$
(4) $C_6H_5OO\cdot + C_6H_6 \rightarrow C_6H_5OOH + C_6H_5\cdot$
(5) $C_6H_5OOH \rightarrow C_6H_5O\cdot + HO\cdot$
(6) $C_6H_5O\cdot + C_6H_5CHO \rightarrow C_6H_5OH + C_6H_5CO\cdot$
(7) $C_6H_6 + HO\cdot \rightarrow C_6H_5\cdot + H_2O$
(8) $C_6H_5\cdot + C_6H_5CHO \rightarrow C_6H_6 + C_6H_5CO\cdot$ Benzaldehyde is rapidly oxidized to a reactive phenyl radical and carbon monoxide as shown in reactions (1) and (2). During the oxidation of phenyl radical, several reactive radicals are generated which react with the benzene generated to generate additional phenyl radicals. These reactive radicals are $C_6H_5OO\cdot$, and $HO\cdot$. The reactions involving these radicals are described in equations (4) – (7). The main reaction sequence leading to phenol formation is the oxidation of phenyl radical shown in reactions (3) to (6).

The oxidation reaction must be carried out at a temperature within the range of about 400° to 600° C., preferably 400° to 500° C. When benzaldehyde and oxygen were preheated together from about a temperature of 210° to about 300° C. at a residence time of 12 seconds, we observed considerable tar formation in the reactor system. These tar deposits were also swept into exit lines and plugged the system. We found that by reducing the residence time of benzaldehyde and oxygen in the preheater to 5 seconds and by raising the temperature at which the reactants are preheated before mixing to 300° to 350° C., tar formation was substantially reduced.

We postulate that at the lower temperatures, between 200° and 300° C., the benzaldehyde reacts with the oxygen to produce perbenzoic acid which in turn reacts with benzaldehyde to produce condensation products which react again with the perbenzoic acid and benzaldehyde to produce tars. We further postulate that at the higher temperatures, between 300° to 400° C., in the presence of oxygen, benzaldehyde reacts to form perbenzoic acid, together with phenyl radicals and carbon monoxide. The phenyl radical, upon contact with the oxygen stream, reacts to form phenol. As the temperature approaches 400° C., less of the perbenzoic acid is formed.

The effect of temperature on benzaldehyde conversion and tar formation also supports this postulation. At 400° C., phenol selectivity increased over that of 300° C. The combined selectivity to phenol, benzene and benzoic acid at 400° C. was between 85 to 90% of the 37% benzaldehyde converted. Combustion and tar formation became minor processes at 400° C.

Product distribution thus is affected by reaction temperature. The combined selectivity to benzene and phenol increased between 300° and 500° C. In the same temperature range, the selectivity to benzoic acid decreased. The overall effect was that the decrease in the selectivity to benzoic acid was accompanied by an increase in the combined selectivity to phenol and benzene.

While we do not wish to be bound by any theory concerning the mechanism of the reduced tar formation, it is theorized that at temperatures above 400° C., the decarbonylation of the benzoyl radical is the key step leading to phenol. Therefore, the overall stoichiometry for the formation of phenol from benzaldehyde is given by the equation $C_6H_5CHO + 1/2O_2 \rightarrow C_6H_5OH + CO$. This equation is consistent also with calculations on the rate of decarbonylation of the acetyl radical in the vapor-phase oxidation of acetaldehyde which have indicated that decarbonylation is the dominant process above 350° C. (R. R. Baldwin and R. Walker, *Fourteenth Symposium on Combustion,* Combustion Institute, Pittsburgh, 243 (1973)). The mole ratio of oxygen/benzaldehyde increases as the reaction proceeds since only half a mole of oxygen is required to oxidize one mole of benzaldehyde to phenol. The rate of reaction with the oxygen therefore increases with an increase in benzaldehyde conversion and the selectivity to phenol increases with attendant reduced selectivity to tar formation.

Unpredictably, the method of mixing the two reactants in the initial step of bringing benzaldehyde and the oxygen-containing gas into intimate contact is a significant factor contributing to tar formation and carbon oxides when oxidizing benzaldehyde to phenol. It would be logically predicted on the basis of the postulated reaction mechanism that to mix the two reactants at 400° C. would minimize tar formation. For reasons which are not understood, mixing of the two reactants, each at 400° C., results in increased formation of carbon oxides and hence lower yields of phenol. It is accordingly readily apparent that methods of manufacturing phenol from benzaldehyde are not predictable and that differences in benzaldehyde to phenol processes exist which are unobvious.

It is therefore essential that the mixing of benzaldehyde and the oxygen-containing gas occur at a temperature below 400° C. The benzaldehyde is preheated in a separate stream to the range of about 300° to 350° C., and the oxygen stream containing an inert diluent is introduced into the mixing chamber at a temperature within the range from about 300° to 350° C. Preferably the benzaldehyde, oxygen and diluent should spend a minimal time in the mixing chamber prior to entering the reactor. The residence time of the reactants in the mixing chamber should not exceed 6 seconds. Reaction conditions are 400° to 600° C., residence time of 0.1 to 10 seconds, and 1 to 10 atmospheres pressure. Tar formation is a factor with residence time over 10 seconds. Preferably, reactor conditions are 400° to 500° C., residence time of 0.1 to 5.0 seconds at atmospheric pressure. Immediately following the reactor is a reaction quench system which brings the process reactants and products to a temperature within the range from about 0° to −80° C.

In operation of the process, that an explosive mixture or the flammability zone be avoided, the benzaldehyde stream is introduced into the reactor system premixed with an inert diluent stream in a concentration sufficient to be outside the explosive limits when the stream is mixed with an oxygen-containing gas. The concentration of benzaldehyde to inert diluent which will avoid an explosive mixture when the mixture is mixed later with oxygen is determined experimentally as the proportions of the non-explosive mixture will vary according to temperature. The inert diluent can be introduced into the benzaldehyde stream, either before or after the benzaldehyde stream has passed through a heating section to bring the benzaldehyde to the desired temperature of 300° to 350° C. The introduction of the diluent can thus be made immediately prior to the reaction chamber which is at 400° to 600° C. After the reactor system has stabilized in temperature, an oxygen-containing stream, also premixed with an inert gas if necessary, is introduced into the benzaldehyde-inert diluent stream until a steady level of phenol product is obtained. The reactor effluent is continuously quenched and condensed at a temperature below 0° C. Phenol is separated from the condensed phase by standard methods such as fractional distillation and solvent extraction. The unreacted benzaldehyde can be separated from the product and substantially recycled back to the reactor. Suitable solvents include water, alcohols such as methyl, ethyl, isopropyl alcohols, and glycols and ethers including dioxane.

In summary, in the vapor-phase decarbonylation processes of this invention, as it applies to benzaldehyde, benzaldehyde is oxidized continuously to phenol in the presence of oxygen-containing gas at 1 to 10 atmospheres pressure at temperatures from 400° to 600° C, but preferably from 400° to 500° C. It is essential that the benzaldehyde, diluted by a non-hydrocarbon inert diluent, be preheated separately to 300° to 350° C. before mixing in the mixing chamber of the reactor to minimize tar formation. Contact maintained within the reactor can be from 0.1 to 10 seconds. Preferably, contact is 0.1 to 5.0 seconds. The reaction is quenched by continuously withdrawing and quenching the reaction products from the said reactor at a temperature below 0° C., typically within the range from 0° to −80° C. The cooled effluent of the reactor is distilled to recover the unreacted benzaldehyde for recycling. Phenol is made in high selectivity (75%) at a 37% benzaldehyde conversion without the use of a hydrocarbon diluent to obtain a 27% yield. To obtain high yields of phenol, it is necessary to operate at temperatures above 400° C using an oxygen:benzaldehyde mole ratio greater than 0.5:1. The said conversion of benzaldehyde to phenol from an equipment standpoint can be carried out in plug-flow as well as back-mixed reactors.

In order to facilitate a clear understanding of the invention, i.e., the novel decarbonylation process to make phenol from benzaldehyde in the absence of a hydrocarbon diluent, the following specific embodiments are described in detail. It should be understood, however, that the detailed expositions of the application of the invention, while indicating preferred embodiments, are given by way of illustration only since various changes and modifications within the spirit and scope of the invention will become apparent to those skilled in the art from this detailed description.

EXAMPLE I

An oxidation reactor which comprised a Vycor tube having an inner diameter of 1 inch and a length of 6 inches was mounted in a vertical position in an electric furnace. The reactor was equipped with means for measuring internal temperature.

Communicating with the upper end of the reactor was a mixing section consisting of a reaction tube approximately 6.75 inches long which was heated by the electric furnace. Connected to the top of the mixing section was a 7.75 inch inlet tube heated by heating tape to a temperature of 300° to 350° C. for introducing the benzaldehyde. The inert diluent and oxygen-containing gas were introduced into the 6.75 inch preheat zone immediately prior to the top of the reactor. The bottom of the reactor had an exit line with an inside diameter of 0.3 inches. This line was connected to a receiver chain consisting of three 500 milliliter flasks in series immersed in a dry ice bath.

In the operation of the reactor, benzaldehyde was vaporized into a stream of nitrogen in a ratio of 1.0 moles benzaldehyde per 10.5 moles of nitrogen by means of a sparge system immersed in a constant temperature bath. The bath was controlled to within ±0.1° C in order to control the concentration of benzaldehyde in the nitrogen stream leaving the sparger. The benzaldehyde-containing nitrogen stream passed through the preheat section of the reactor system. The benzaldehyde and the oxygen-inert diluent mixture were preheated to 300° C prior to their introduction into the mixing section. Molecular oxygen was introduced into the mixing section at a controlled rate of 2.0 moles of oxygen per 1.0 mole of benzaldehyde.

Into the reactor, operating as discussed above at a temperature of 400° C and at atmospheric pressure, there was continuously introduced 0.069 moles per hour of benzaldehyde and 0.72 moles per hour of nitrogen, together with 0.14 moles per hour of oxygen.

The reactor was operated in this manner for over 5 hours. The condensed products were accumulated in the receiver flask chain of three 500 ml flasks immersed in a dry ice acetone bath. Analysis of the products was carried out by gas chromatography. Tar was determined by weighing the reactor tube after the run.

Table I gives the reaction conditions and the results obtained. Phenol selectivity is based upon the amount of benzaldehyde reacted and is defined as:

$$\text{Phenol Selectivity, \%} = \frac{\text{moles of phenol formed}}{\text{moles of benzaldehyde reacted}} \times 100$$

TABLE I
BENZALDEHYDE CONVERSION TO PHENOL
EXAMPLE I

| Reactor Conditions Feed | Mole Ratio |
|---|---|
| Benzaldehyde | 1.0 |
| Oxygen | 2.0 |
| Nitrogen | 10.5 |
| Total | 13.5 |
| Reaction Temperature | 400° C |
| Contact Time | 4 seconds |
| Reactor Results | |
| Selectivity | Mole % |
| Phenol | 75 |
| Benzene | 3 |
| Benzoic Acid | 8 |
| Tar | 7 |
| Combustion | 7 |
| Conversion Per Pass - Benzaldehyde | 37% |
| Yield Per Pass - Phenol | 27.4 Mole % |

EXAMPLE II

The reaction system utilized in Example I was modified to add an 7.75 inch preheat zone prior to the 6.75 inch preheat zone of the reactor. The oxygen-nitrogen stream and the benzaldehyde stream were introduced in the reactor at the top of the 7.75 inch preheat zone and permitted to mix intimately. The 7.75 inch preheat zone was heated with heating tape to 200°-216° C. The second preheat zone of 6.75 inch in length was heated by the furnace to 308° C. The 6 inch reaction zone at the bottom of the Vycor tube was heated to 400° C. With this apparatus, the benzaldehyde and oxygen mixture spent a total residence time of 12.3 seconds in the 14.5 inch preheat zone, increased from the 5.2 seconds residence time of Example I.

When the reactor was operated with the 14.5 inch preheat section at a 12.3 second residence time, we observed considerable amounts of tar and carbonaceous deposits in the preheat zone which also was swept into the reactor and exit lines. The quantity of tar formed was such that the reactor became inoperable after a few minutes of operation.

EXAMPLES III to XIV

The same reaction system described in Example I was employed. Benzaldehyde and oxygen mole ratios, reaction temperature and contact time in seconds were varied within limits to determine the effects of such variations. The oxidations were carried out at reactor feeds of one mole of benzaldehyde with 0.8 to 2.6 moles of oxygen, at temperatures within the range of 300° to 500° C and contact times from ½ to 4 seconds. As Examples III through XIV indicate, benzoic acid decreased with an increased reaction temperature from 300° to 500° C.

TABLE II
EXAMPLES III - XIV - Reaction Data

| Ex. | Contact Time, Sec. | Reaction Temp., °C.* | Benzaldehyde Conversion Per Pass | Reaction Products** Selectivity, Mole % | | | Phenol/Yield/ Pass, Mole % | Reactor Feed Mole Ratio | | |
|---|---|---|---|---|---|---|---|---|---|---|
| | | | | Phenol | Benzene | Benzoic Acid | | $\phi$CHO | $O_2$ | $N_2$ |
| III | 2 | 300 | 25 | 30 | 19 | 8 | 7.5 | 1 | 2.4 | 13.9 |
| IV | 2 | 350 | 23 | 42 | 22 | 10 | 9.8 | 1 | 2.2 | 13.0 |
| V | 2 | 400 | 19 | 59 | 17 | 2 | 11.5 | 1 | 2.6 | 13.7 |
| VI | 1 | 400 | 14 | 62 | 27 | 1 | 8.5 | 1 | 2.6 | 13.7 |
| VII | 4 | 400 | 28 | 69 | 3 | 3 | 19.4 | 1 | 2.3 | 12.0 |
| VIII | 1 | 400 | 21 | 55 | 19 | 3 | 11.7 | 1 | 0.8 | 5.1 |
| IX | 2 | 400 | 17 | 46 | 28 | 4 | 7.8 | 1 | 1.4 | 17.6 |
| X | 1 | 450 | 17 | 60 | 23 | 1 | 9.8 | 1 | 2.2 | 11.5 |
| XI | ½ | 500 | 56 | 31 | 32 | 1 | 17.5 | 1 | 0.9 | 5.1 |
| XII | ½ | 500 | 52 | 29 | 29 | 1 | 14.7 | 1 | 0.9 | 11.9 |
| XIII | 1 | 500 | 87 | 9 | 16 | 1 | 7.8 | 1 | 2.5 | 13.3 |
| XIV | 1 | 500 | 65 | 23 | 21 | 1 | 14.8 | 1 | 1.1 | 14.2 |

*Atmospheric pressure
**Other products formed included water, carbon oxides and tar

EXAMPLE XV

The following illustrates the increased formation of tar and carbon oxides when the two streams of benzaldehyde, the oxygen-containing gas and inert diluent were brought together at 400° C.

An experiment was carried out to determine whether phenol selectivity could be improved by preheating separately the benzaldehyde and oxygen-containing stream and allowing the preheated streams to mix at 400° C.

Accordingly, a stream containing benzaldehyde and nitrogen in a mole ratio of 0.36:1 was allowed to mix at 400° C. with a stream containing oxygen and nitrogen in a mole ratio of 0.27:1. The overall mole ratio of benzaldehyde:oxygen:nitrogen was 1:1.8:9.6.

Into a Vycor double cone back-mixed reactor consisting of a mixing cone with a base of 2 cm and a height of 2.5 cm and a reactor cone with a base of 4 cm and a height of 7.5 cm with a 4 mm orifice separating the mixing cone from the reactor cone, and which was maintained at atmospheric pressure, there was continuously introduced benzaldehyde vapor, oxygen and nitrogen, each stream at 400° C. Reactions were carried out in the temperature range of 400° C. with heat being supplied by an electric furnace. The vapors leaving the reactor were condensed at −70° C. The product mixture was allowed to warm up to room temperature whereby the products were separated and analyzed by gas chromatography. Table III indicates the decrease in phenol selectivity and increase in tar and carbon oxides formation versus that shown in Table I.

TABLE III
BENZALDEHYDE CONVERSION TO PHENOL
EXAMPLE XV

| Reactor Conditions Feed | Mole Ratio |
|---|---|
| Benzaldehyde | 1.0 |
| Oxygen | 1.8 |
| Nitrogen | 9.6 |
| Total | 12.4 |
| Reaction Temperature | 400° C. |
| Contact Time | 2.9 seconds |
| Reactor Results | |
| Selectivity | Mole % |
| Phenol | 33.5 |
| Benzene | 9.7 |
| Tar and Carbon Oxides | 56.4 |

TABLE III-continued

BENZALDEHYDE CONVERSION TO PHENOL
EXAMPLE XV

| | |
|---|---|
| Conversion Per Pass - Benzaldehyde | 32.4% |
| Yield Per Pass - Phenol | 10.8 Mole % |

What is claimed is:

1. A continuous process for the production of phenolic compounds from aromatic aldehydes having the chemical formula RCHO wherein R is selected from the group consisting of phenyl, biphenyl, naphtyl, anthacyl and phenanthryl radicals, which comprises the step of (1) continuously premixing in a preheat zone a composition consisting essentially of oxygen-containing gas, said aldehyde and inert gaseous diluent at a temperature of about 300° to 350° C wherein said inert gaseous diluent is selected from the group consisting of nitrogen, argon, steam, carbon dioxide and mixtures thereof and is present in a concentration sufficient for said composition to be outside the explosive limits, (2) continuously introducing said composition into a reactor and reacting said aldehyde and said oxygen-containing gas at a temperature of from about 400° to 600° C in the vapor phase in mole ratios of from 0.4 to 1 to 40 to 1 in said reactor maintained at 1 to 10 atmospheres pressure, maintaining said reactants in said reaction chamber for up to 10 seconds, thereby converting at least a portion of said aldehyde to phenolic compounds, and (3) quenching the reaction by continuously withdrawing and quenching the reaction products from said reactor at a temperature of from about 0° to about −80° C.

2. The process of claim 1 wherein said aldehyde comprises benzaldehyde.

3. The process of claim 1 wherein said oxygen-containing gas comprises oxygen.

4. The process of claim 1 wherein said aldehyde comprises benzaldehyde and said oxygen-containing gas comprises oxygen.

5. The process of claim 4 wherein the mole ratio of oxygen to benzaldehyde is within the range of from 0.4 to 3.0 moles of oxygen per mole of benzaldehyde.

6. The process of claim 1 wherein said reaction temperature comprises from about 400° to 500° C.

7. The process of claim 1 wherein residence time of said feedstocks in said reactor comprises from about 0.1 to 5 seconds.

8. The process of claim 1 wherein said reaction products are separated from unreacted feedstocks.

9. The process of claim 1 wherein said separated unreacted feedstocks are recycled for continuous preheating before being reintroduced into said reactor.

10. The process of claim 1 wherein said diluent is present in a mole ratio within the range from about 2.0 to 50 moles per mole of benzaldehyde.

11. The process of claim 2 wherein phenol is isolated from the reaction product as step (4).

* * * * *